United States Patent [19]

Akins et al.

[11] 4,126,924
[45] Nov. 28, 1978

[54] SOCKET AND JOINT PROSTHESES

[75] Inventors: Robert J. Akins, La Mesa; Victor Slivenko, San Diego, both of Calif.

[73] Assignee: General Atomic Company, San Diego, Calif.

[21] Appl. No.: 766,024

[22] Filed: Feb. 7, 1977

[51] Int. Cl.² ............................................. A61F 1/24
[52] U.S. Cl. ...................................... 29/423; 29/447; 29/458; 29/527.2; 3/1.912; 128/92 C; 427/2
[58] Field of Search ..................... 29/441 R, 446, 447, 29/527.2, 423, 453, 424, 425; 3/1.912, 1.913; 128/92 R, 92 C, 92 CA; 427/2, 185, 398 R

[56] References Cited

U.S. PATENT DOCUMENTS

| | | | |
|---|---|---|---|
| 3,526,005 | 9/1970 | Bokros et al. | 128/92 R X |
| 3,677,795 | 7/1972 | Bokros et al. | 427/2 |
| 3,707,006 | 12/1972 | Bokros et al. | 128/92 CA X |
| 3,813,699 | 6/1974 | Giliberty | 3/1.912 |
| 3,894,297 | 7/1975 | Mittelmeier et al. | 3/1.912 |
| 3,896,547 | 7/1975 | Kulwiec | 128/92 C X |

Primary Examiner—Michael J. Keenan
Attorney, Agent, or Firm—Fitch, Even, Tabin & Luedeka

[57] ABSTRACT

Pyrolytic carbon artificial socket prostheses for permanent or prolonged implantation in a living body, and methods for making such prostheses. The prostheses comprise a suitably shaped socket element substrate having a hemispherical socket cup, a compression-loaded hemispherical carbon shell mounted in said cup, and a vapor deposited carbon coating (including carbon-carbon alloys) on the substrate-carbon shell assembly.

1 Claim, 4 Drawing Figures

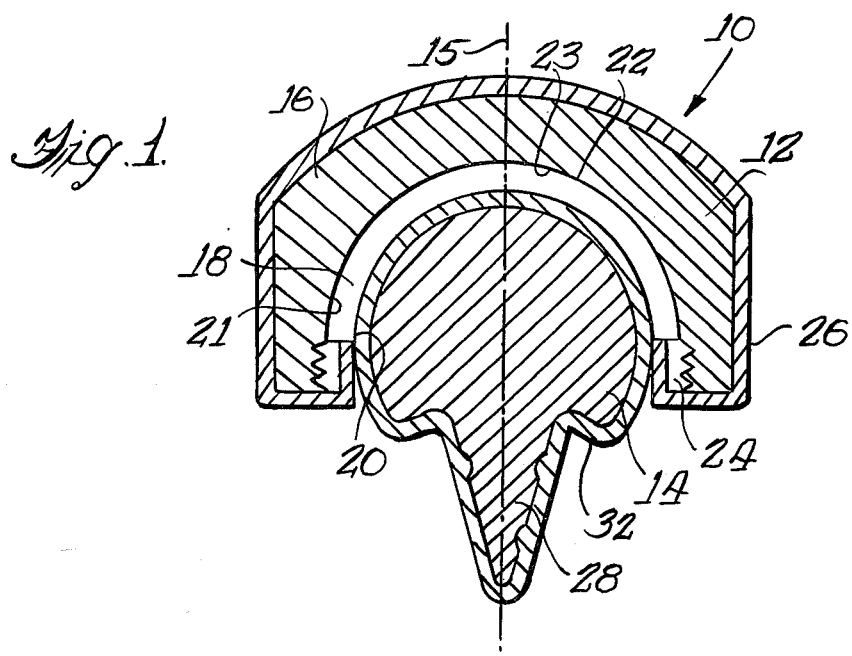
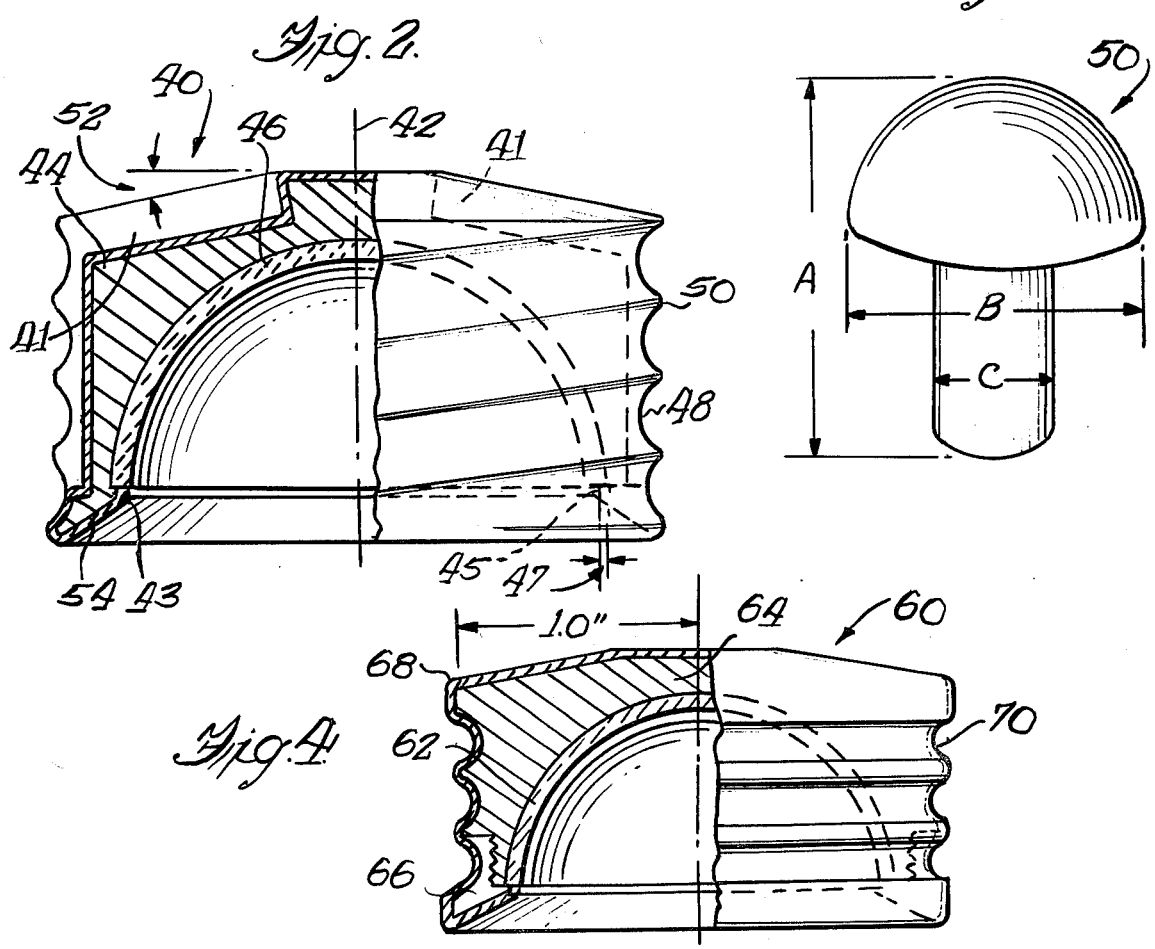

SOCKET AND JOINT PROSTHESES

The present invention relates to prosthetic devices designed for use in orthopedics. More particularly, the present invention relates to orthopedic joint prostheses and to the manufacture of such prostheses.

One requirement for a satisfactory prosthetic device which is to be permanently implanted in a living body is that it be physiologically inert for indefinite periods of time. Various difficulties with conventional ball joint prostheses, such as those fabricated from metal and/or plastic, are that materials from which they are constructed may be physiologically rejected, may cause inflammation of bodily tissue, may exhibit poor wear characteristics, may cause damage to any remaining, natural bone structure or may be degraded by bodily processes.

Improved pyrolytic carbon coated prostheses, including improved ball joint prostheses, have more recently been provided, as described in U.S. Pat. Nos. 3,526,005 and 3,707,006. Such prostheses are biologically inert, have exceptional wear characteristics, and may be provided with a modulus of elasticity approximating that of natural bone and other properties which facilitate permanent or prolonged structural implantation.

However, there are some difficulties in connection with providing spherical pyrolytic carbon coated sockets for ball joint prostheses because of limited coating thickness or uniformity provided in hemispherical depressions.

It is an object of the present invention to provide improved ball joint prostheses for prolonged or permanent implantation in a living body. Another object is to provide improved ball joint prostheses having a thick pyrolytic carbon layer at the internal socket surface. These and other objects of the invention are more particularly set forth in the following detailed description and in the accompanying drawings of which FIG. 1 is a cross-sectional side view of a hip joint ball and socket prothesis.

FIG. 2 is a side view, partially broken away, of the socket portion of another embodiment of a hip joint ball and socket prosthesis.

FIG. 3 is a perspective view of a hemispherical coating substrate form for manufacturing the hemispherical pyrolytic carbon socket shells of the prostheses of FIGS. 1 and 2, and FIG. 4 is a side view, partially broken away, of another embodiment of a hip joint socket prosthesis.

Generally, the present invention is directed to socket prostheses for implantation in a living body, which have a thick, pyrolytic carbon articulating socket surface, and to methods for manufacturing such socket prostheses. The invention is also directed to matching ball prostheses having pyrolytic carbon articulating ball surfaces.

In accordance with the methods of the present invention, a deposition shell form substrate is provided having a hemispherical deposition surface zone. The surface of the deposition zone desirably has a predetermined hemispherical shape generally corresponding to the intended shape of the prosthesis socket articulation surface, as will be described in more detail hereinafter. A thick pyrolytic carbon coating shell is deposited at elevated temperature on the deposition zone surface and, in this connection, the pyrolytic carbon coating shell should have a thickness of at least about 0.80 millimeters. The shell form substrate will generally have a coefficient of thermal expansion greater than the coefficient of thermal expansion of the pyrolytic carbon coating on the substrate, and upon cooling the pyrolytic carbon coated substrate deposition surface zone, the coating shell is held in compressive strain for reasons which will also be described in more detail hereinafter.

Also in accordance with the present invention, a socket cup substrate is provided having an exterior shape adapted for hip implantation, and having a hemispherical socket cavity with an inner socket surface conforming to the outer surface of the pyrolytic carbon coated deposition zone of the substrate. The socket substrate may also be provided with means for retaining the pyrolytic carbon coated deposition zone surface in the socket cavity. The retaining means should be capable of holding the coating shell under compression in the cup socket. A particularly preferred retaining means comprises an inwardly projecting lip for press-fit locking of the pyrolytic carbon coating shell in the cavity.

Further in accordance with the method, the deposition form substrate material is then removed from the inside of the pyrolytic carbon shell. This expands the shell to fit tightly against the inside surface of the socket substrate, including the retaining means of the socket cup. This substrate material removal also produces the articulating socket region of the prosthesis which receives the articulating ball surface. The cup-shell assembly is then coated with pyrolytic carbon preferably after removal of the shell form substrate material, to provide an integral hip socket joint prosthesis, which may be finished to the final dimensions and surface configuration desired. The pyrolytic carbon coating applied to the assembly will generally be at least about 0.51mm thick, and preferably will be in the range of from about 0.76mm to about 1.0mm in thickness. In this latter connection, the socket surface will be generally finished to a highly polished hemispherical surface configuration matching that of the corresponding ball joint surface of the ball joint prosthesis element. The ball element of a ball and joint prostheses may be provided by carbon deposition on a suitable ball element substrate. Surfaces of the prosthesis intended to be implanted in natural bone tissue may be provided with a degree of surface or modification appropriate to such implantation.

As indicated, the present invention involves the provision of carbon coatings or layers on appropriate substrates, and in this connection, the deposition of the pyrolytic coatings may be carried out by conventional deposition methods, such as discussed in U.S. Pat. Nos. 3,526,005 and 3,707,006, which are assigned to the assignee of the present invention.

It is desirable that pyrolytic carbon shells and coatings have a high degree of isotrophy, and a certain density value and other properties. In this connection, anisotropic carbon coatings tend to delaminate when complex shapes are cooled after depositing the pyrolytic carbon at high temperatures. For coating complex shapes (i.e., those having a radius of curvature less than ¼" at some portion), the pyrolytic carbon should best have a Bacon Anisotrophy Factor (BAF) of not more than about 1.3. The BAF is a conventional measure of preferred orientation in the layer planes in the carbon crystalline structure. For non-complex shapes, higher BAF values of less than about 2.0 should still best be used.

The density of the pyrolytic carbon socket shell, and pyrolytic carbon coatings of socket and ball element surfaces, is related to various mechanical properties, and further relates, in part, to the thermal expansion properties utilized in the manufacture of the socket portion of the prostheses in accordance with the present invention. The pyrolytic carbon of the coatings and socket shell and shell should have a density of at least about 1.5 grams per cubic centimeter, and preferably the pyrolytic carbon should have a density between about 1.9 and about 2.2 grams per cubic centimeter. Furthermore, the pyrolytic carbon of the coatings and socket shell should best have a coefficient of thermal expansion in the range of from about $4.0 \times 10^{-6}/°$ C. to about $6.0 \times 10^{-6}/°$ C. and more preferably about $6 \times 10^{-6}/°$ C.

A further characteristic of the carbon which affects various of its properties is the crystallite height or apparent crystallite size. Pyrolytic carbon coatings and socket shells should best be provided with a crystallite size no greater than about 200 Angstroms. In general, the desirable characteristics of pyrolytic carbon for use in prosthetic devices are greater when the apparent crystallite size is small, and preferably the apparent crystallite size should be between about 20 and about 50 Angstroms.

Since this substrate material for the ball and socket joint prostheses will preferably be completely encased in pyrolytic carbon, the choice of the material from which to form the substrate is not of utmost importance per se. However, the substrate material should have suitable mechanical strength and structural properties for joint prosthesis use, and should be compatible with pyrolytic carbon elevated temperature conditions for its deposition. In the pyrolytic carbon deposition by thermally induced decomposition of a hydrocarbon gas, temperatures of about 1,000° C. or more may be used. The pyrolytic carbon may be deposited either with or without the additional inclusion of materials, such as carbide-forming elements, in accordance with known techniques. Temperatures of pyrolytic carbon deposition below about 1,500° C. are particularly suited for coatings to be used in prosthetic devices.

Because the substrate may be coated at relatively high temperatures, the coefficients of thermal expansion of substrate and of the pyrolytic carbon deposited thereon should be relatively close to each other so the pyrolytic carbon may be deposited on the substrate with establishment of a bond therewith which may be maintained upon cooling of the coated assembly, without destruction to the coating or substrate. For the shell form substrate on which the pyrolytic carbon socket shell is deposited, the difference between the coefficient of thermal expansions of the substrate and the deposited carbon layer should be sufficient to provide a compressive strain in the pyrolytic carbon layer of at least about 3% upon cooling from the deposition temperature to the fabrication temperature (which will ordinarily be room temperature). The substrate material for the ball elements (and the socket elements) of the prostheses should combine with the coating to provide the final pyrolytic carbon part with a modulus of elasticity approximating that of natural bone. Particularly desirable substrate materials for both the shell form substrate and the socket elements and ball element substrates are artificial isotropic graphites, such as polycrystalline graphites having a density of about 1.85 g/cm³ and a coefficient of thermal expansion in the range of from about 7.0 $\times 10^{-6}/°$ C. to about $8 \times 10^{-6}/°$ C. A preferred substrate material is Poco AXF-9Q graphite. Such artificial graphites may be provided with a modulus elasticity in the range of the modulus elasticity of natural bone. For example, particularly preferred forms of graphite for use as substrate material is polycrystalline graphites having a modulus of elasticity in the range of from about 1.4 to about $1.6 \times 10^6$ psi. An example of such graphite is the polycrystalline graphite sold under the tradename Poco AXF-5Q graphite, which has a density of about 1.85 grams per cubic centimeter, an average particle size of about 0.025mm an isotrophy of nearly 1.0 on the Bacon scale, and a modulus of elasticity of about $1.6 \times 10^6$ psi.

The pyrolytic carbon coating may be applied to the substrate using conventional pyrolytic carbon deposition apparatus. Preferably, an apparatus is utilized which maintains a substrate in motion while the coating process is carried out, to provide for uniform distribution of the coating on the desired surfaces of the substrate. When the substrates to be coated are small enough to be levitated in an upwardly flowing gas stream, a fluidized bed coater is preferably used. When larger substrates are employed, or where it is desired to vary the thickness or other characteristics of the pyrolytic carbon coating over different portions of the substrate, different coating methods may be employed, such as supporting the substrate on a rotating or stationary mandrel within a large fluidized bed. A rotating drum coater or a vibrating table coater may also be employed.

Turning now to the drawings, various aspects of the invention will be further described in respect of the embodiments of FIGS. 1 and 2.

In FIG. 1, there is illustrated a hip joint prosthesis 10 embodiment comprising a socket element 12, and a mating ball element 14. The drawing is shown as a cross-section through axis of symmetry 15, and it is to be understood that the illustrated ball and socket elements are radially symmetrical about the axis 15. The socket element 12 is adapted for suitable implantation in the hipbone of a living person, and comprises graphite substrate 16 fabricated from a polycrystalline isotropic graphite material having a density of 1.85 g/cm³, a modulus of elasticity of $1.6 \times 10^6$ psi and a coefficient of thermal expansion of $7.7 \times 10^{-6}/°$ C. which is sold under the trade designation Poco AFX-5Q. The exterior surface of the graphite substrate 16 is shaped to provide for implantation in a suitably prepared implantation site (surgically prepared at the former hip socket location). The graphite substrate 16 is also provided with a hemispherically-shaped cup recess 21 for receiving a generally hemispherical socket shell 18, and, in this regard, the shape of the inner surface 23 of cup recess 21 conforms with the shape of the outer surface 22 of the socket shell 18 for a precise fit of the shell 18 therein. The generally hemispherical pyrolytic carbon socket shell is of generally uniform radial thickness and has a highly polished hemispherical inner surface 20. The socket shell 18 has a radial thickness of about 0.76 mm., a coefficient of thermal expansion of about $6.0 \times 10^{-6}/°$ C. (20° C.) and a density of about 2.2 g/cm³.

The socket element 12 further includes a threaded retaining ring 24 at the distal end of the socket element having an inner diameter smaller than the outer diameter of the socket shell 18, and which holds the pyrolytic carbon socket shell 18 under compression in the cup recess 21 against the recess surface 23. The ring 24 is in threaded engagement with the distal end of the substrate 16 and is also affixed by means of an exterior pyrolytic carbon coating 26.

As indicated, the socket element 12 is also provided with an exterior pyrolytic carbon coating 26, which, in illustrated embodiment, has a thickness of about 0.76mm. The pyrolytic carbon coating 26 has an as-deposited surface roughness which facilitates firm affixation to the hipbone at the implantation site. As previously indicated, however, the interior surface 23 of the socket element 12 is highly polished to provide for reduced friction and wear upon movement therein of the ball element 14.

Like the socket element 12, the ball element 14 of the prosthesis 10 comprises a graphite substrate 28 fabricated from the same polycrystalline Poco AXF-5Q graphite material from which the socket substrate is formed. The distal, articulating end of the ball has a spherically-shaped surface with a solid angle greater than 2 pi radians to provide for movement in the hemispherical socket shell 18, while maintaining full surface contact with the shell 18. The proximate end of the ball element substrate 28 is generally conical in shape, and the conical proximate end and the spherical distal end join with a recessed contour which provides a frustroconical surface 32 surrounding the conical end with an inclination opposite that of the conically-shaped, centrally-positioned end portion. For implantation of the ball element, the ball is centered into a metal stem in an offset manner like that of the natural ball joint element, which in turn is fastened to the femur shaft in a conventional manner.

The ball element substrate 28 is, like the socket element, provided with a pyrolytic carbon coating having a thickness of about 0.50mm and a density of about 2.2g/cm$^3$. The conical implantation surface of the ball element, like the implantation surface of the socket element, is permitted to retain the as-deposited surface roughness of the deposition process. The surface may also be provided with physical and/or chemical surface modification as disclosed in U.S. Pat. No. 3,707,006, if desired.

The outer surface of the articulating ball surface of the ball portion is highly polished, and the diameter of the ball surface matingly corresponds to the inner diameter of the concave hemispherical surface of the socket portion 12 of the joint prosthesis 10, so that these two surfaces match in functional joint relationship, and coact with low friction and wear characteristics.

Illustrated in FIG. 2 is another embodiment of a joint prosthesis socket element 40. The socket element 40 of FIG. 2 is shown in side view, partially broken away along a vertical plane intersecting the axis 42 of radial symmetry of the socket element. Like the socket element 12 of FIG. 1, the socket element comprises a graphite substrate 44 fabricated from Poco AXF-5Q graphite, and having a socket cup with an internal radius that is the same as that of the hemispherical pyrolytic carbon shell 46. The shell 46 is retained under compression in the socket cup cavity, at least in part, by a press-fit retainer ring 43, which is an integral part of the substrate 42. The ring 43 has a thickness 45 of 0.017 inches and projects radially inwardly from the substrate cup surface a distance 47 of 0.004 inches. The pyrolytic carbon shell 46 has a thickness of 0.76mm, a density of 2.2 g/cm$^3$, a BAF of less than 2.0 and a crystallite size of about 40 angstroms. The cylindrical exterior implantation surface 48 of the substrate 44 is also provided with screw threads 50 (four threads per inch) to facilitate implantation in threaded engagement with the natural bone implantation site. The proximate end of the implantation surface is further provided with a tapered frustroconical surface at a 10° inclination angle 52. At the distal end of the socket element, the substrate 46 has a frustroconical surface 54 which flares from the retaining ring 43 at an angle of 30° to accommodate ball joint movement in the socket element.

As indicated, the pyrolytic carbon shells of the socket elements of the embodiments of FIGS. 1 and 2 are held in compression in the substrate socket cups. The manufacture of the socket shells and their assembly will now be more particularly discussed in connection with the following description of the method manufacture of the socket element embodiment 40, illustrated in FIG. 2.

Illustrated in FIG. 3 is a shell substrate form 50 which is machined from Poco AXF-5Q graphite having a coefficient of thermal expansion of $8 \times 10^{-6}/°$ C. The form 50 is machined to have a radius 0.005 inch less than the femur head finish diameter of the ball element to be used therewith. In the illustrated embodiment, the form 50 has indicated dimensions "A" of 1.729 inches, "B" of 1.400 inches, and "C" of 0.490 inches, all at room temperature. The shell substrate form is subsequently coated in a fluidized coating bed in accordance with conventional procedures such as discussed in the previously referred to patents to produce a good coating having relatively smooth surfaces and a pyrolytic carbon coating thickness of about 0.80 mm on the hemispherical shell surface. At a deposition temperature of about 1400° C. the respective A, B, C dimensions of the substrate are as follows:

$A = 1.747$ inch $B = 1.415$ inch $C = 0.495$ inch

The pyrolytic carbon coating is applied, and is stress free at the coating temperature of about 1400° C. (In respect of the diameter dimension "B" of the substrate, which is 1.4 inches at room temperature, at 1400°, the polycrystalline substrate graphite has expanded by 1.400 inches times $8 \times 10^{-6}/°$ C. times about 1400° C., or about 0.016 inches. The pyrolytic carbon has a thermal expansion coefficient of about $6 \times 10^{-6}/°$ C., and thus contracts only about 0.012 inches upon cooling from 1400° C.) However, when the pyrolytic carbon-coated graphite substrate is cooled to fabrication temperature, which ordinarily will be room temperature, the difference in the thermal expansion coefficients between the pyrolytic carbon coating and the graphite substrate places the coating in compression. In this connection, if the pyrolytic carbon coating is permitted to cool to room temperature by itself, it would contract by $6 \times 10^{-6}/°$ C. $\times$ 1.4 $\times$ 1400 = 0.012 inches. At room temperature, accordingly, since the substrate is much thicker than the coating, the pyrolytic carbon shell is driven into elastic compressive deflection by an amount substantially equal to the difference between the contraction of the carbon and the substrate, or, as in the case of the illustrated embodiment, 0.016 inches — 0.012, or 0.004 inches. Of course, the graphite substrate should not be stressed beyond its tensile failure stress. The relative coefficients of thermal expansion of the substrate and coating and the other physical properties of these materials may be slected to provide a desired degree of compressive strain in the pyrocarbon shell without substrate failure. This compressive deflection is recoverable when the graphite substrate is removed.

The coated substrate is cut along a diameter plane, as indicated in FIG. 3, and is subsequently pressed at room temperature into the socket portion of a machined artificial isotropic graphite substrate as shown in FIG. 2. As previously discussed, in the illustrated embodiment of FIG. 2, the substrate has a retaining ring lip 43 for retaining the shell in the socket while the shell graphite is being removed, and the cut hemispherical substrate shell is press-fit into the socket cavity, past the ring lip 43. The lip ring 43 projects radially inwardly a distance which provides an opening diameter less than the coated diameter of the hemispherical shell-substrate assembly, but which permits insertion of the hemispherical shell and substrate assembly, without compressive failure of the ring 43. Suitable lip dimensions may be determined as follows: The approximate tensile strain at fracture for the Poco AXF-5Q graphite substrate is 0.8%, or 0.008 inch/inch. The inside diameter of the socket is equal to the outside diameter of the shell-substrate assembly, 1.4 inches, plus 0.070 inch coating thickness allowance. The deflection of the lip at fracture (0.8% tensile strain) may be estimated as follows:

$$(1.47 \cdot \pi) + (1.47 \cdot \pi \cdot .008) = 4.655$$

$$\frac{4.655}{\pi} = 1.482$$

$$1.482 - 1.47 = 0.0117$$

$$\frac{.0117}{2} = .0059 \text{ (Lip dimension that will result in fracture)}$$

After having been press-fit into the socket shell, all but 0.01 inch layer of the substrate graphite is subsequently removed from the pyrocarbon shell by matching. This thin layer aids in the final machining of the socket cavity.

The shell socket and shell assembly is subsequently coated in the same fluidized bed pyrolytic carbon coating apparatus. The socket element may be finished and readied for implantation by grinding and polishing the socket cavity and ball surfaces to the allowable tolerances and surface finish so that a low friction ball and socket joint is obtained. As previously indicated, the thin layer of substrate graphite of the socket cavity before pyrolytic carbon coating aids in the final machining and provides for readily exposing the hemispherical inner surface of the pyrolytic carbon substrate shell. The ball element is fastened to a metal stem of appropriate shape that is adapted to be used to attach the ball element to the end of the femur shaft. The ball and socket elements may be implanted by appropriate surgical techniques and procedures.

Another similar embodiment 60 of a ball socket prosthesis is shown, to approximate scale, in FIG. 4, with socket shell 62, substrate 64, threaded retaining ring 66, and pyrolytic carbon coating 68. The grooves 70 on the outer body of the prosthesis are circular rather than spirally threaded, and other implantation stabilization configurations such as outer grooves parallel to the axis of the implant may also be used if desired (such grooves are shown in the embodiment of FIG. 2 at numeral 41). The ball and socket elements have advantages in that a low friction joint is provided that has desirable wear resistant properties, is non-biodegradable in body tissues and has excellent resistance to fatigue failure. The retention of the as-deposited surfaces where the socket element is in contact with the natural bone tissues provides for ingrowth of new bone into the carbon surface, resulting in a very firm attachment that is not compromised during use due, in part, to the close matching of the elastic modulii of the pyrolytic carbon and natural bone. It will be appreciated that through the present invention, there are provided ball and socket joint prostheses elements for permanent or prolonged implantation in a living body. In this connection, while primary reference may generally be made to hip joint prostheses for repair of a living human body, it should also be recognized that the improved joint prostheses may also have veterinary applications.

While the present invention has been described particularly in respect of particular embodiments, it will be appreciated by those skilled in the art that various adaptations, modifications and alterations, may be made without departing from the spirit and scope of the present invention.

Various of the features of the present invention are set forth in the following claims.

What is claimed is:

1. A method for manufacturing socket prostheses for permanent or prolonged implantation in a living body, comprising the steps of depositing a carbon shell on a hemispherical substrate form at elevated temperature, said deposited carbon shell having a coefficient of thermal expansion less than that of said substrate, cooling said substrate form and said carbon shell deposited thereon to place said shell under compressive strain, mounting said hemispherical substrate form and compressively strained shell in a hemispherical socket cavity of a suitably shaped socket element substrate, removing said substrate form from said carbon shell to provide a socket element substrate-carbon shell assembly having said carbon shell as a socket bearing element, and depositing a carbon coating on said socket element substrate-shell assembly.

* * * * *